United States Patent
Fine et al.

(10) Patent No.: US 8,701,657 B2
(45) Date of Patent: Apr. 22, 2014

(54) SYSTEMS FOR GENERATING NITRIC OXIDE

(75) Inventors: David H. Fine, Cocoa, FL (US);
Gregory Vasquez, Cocoa, FL (US);
Bryan Johnson, Merritt Island, FL (US)

(73) Assignee: Geno LLC, Cocoa, FL (US)

( * ) Notice: Subject to any disclaimer, the term of this patent is extended or adjusted under 35 U.S.C. 154(b) by 125 days.

(21) Appl. No.: 12/541,141

(22) Filed: Aug. 13, 2009

(65) Prior Publication Data
US 2010/0043789 A1 Feb. 25, 2010

Related U.S. Application Data

(60) Provisional application No. 61/090,616, filed on Aug. 21, 2008.

(51) Int. Cl.
*A61M 15/00* (2006.01)
*A61M 16/00* (2006.01)
*A62B 7/08* (2006.01)
*A62B 21/00* (2006.01)

(52) U.S. Cl.
USPC ............ 128/202.26; 128/204.18; 128/203.12

(58) Field of Classification Search
USPC ............ 128/202.26, 203.12, 203.22, 204.14, 128/204.18, 205.25; 95/128, 129; 422/120, 422/122, 129, 177; 423/402
See application file for complete search history.

(56) References Cited

U.S. PATENT DOCUMENTS

| | | | | |
|---|---|---|---|---|
| 2,127,561 A * | 8/1938 | Herrmann | | 422/160 |
| 3,272,336 A * | 9/1966 | Humbert, Jr. | | 210/132 |
| 4,256,101 A * | 3/1981 | Ellestad | | 128/204.23 |
| 4,374,094 A * | 2/1983 | Farnham | | 422/218 |
| 4,459,982 A * | 7/1984 | Fry | | 128/204.23 |
| 4,602,653 A * | 7/1986 | Ruiz-Vela et al. | | 137/88 |
| 5,514,205 A * | 5/1996 | Awaji | | 96/152 |
| 5,752,506 A * | 5/1998 | Richardson | | 128/204.18 |
| 6,758,214 B2 * | 7/2004 | Fine et al. | | 128/203.12 |
| 7,040,313 B2 * | 5/2006 | Fine et al. | | 128/203.12 |
| 7,520,280 B2 * | 4/2009 | Gordon | | 128/205.28 |
| 2001/0035186 A1* | 11/2001 | Hill | | 128/204.18 |
| 2003/0106554 A1* | 6/2003 | de Silva et al. | | 128/204.22 |
| 2004/0081580 A1* | 4/2004 | Hole et al. | | 422/44 |
| 2006/0048779 A1 | 3/2006 | Rounbehler et al. | | |
| 2006/0180147 A1* | 8/2006 | Rounbehler et al. | | 128/203.12 |
| 2006/0283447 A1 | 12/2006 | Dhuper et al. | | |
| 2007/0144515 A1* | 6/2007 | Stenzler et al. | | 128/203.25 |
| 2007/0181126 A1* | 8/2007 | Tolmie et al. | | 128/204.21 |
| 2010/0025091 A1* | 2/2010 | Ferdinandi et al. | | 174/257 |

OTHER PUBLICATIONS

Miller, Celermajer, Deanfield, Macrae. Guidelines for the safe administration of inhaled nitric oxide. 1994. Archives of Disease in Childhood. vol. 70. pp. F47-F49.*

* cited by examiner

*Primary Examiner* — Rachel Young
(74) *Attorney, Agent, or Firm* — Steptoe & Johnson LLP

(57) ABSTRACT

In one aspect, a system for delivering nitric oxide to a patient can include a first gas source including nitrogen dioxide mixed in air or oxygen, a second gas source supplying compressed air, a ventilator coupled to the first and second gas sources, where the ventilator can be resistant to nitrogen dioxide, and where the ventilator provides a gas flow having a proper amount of nitrogen dioxide, one or more conversion devices operably coupled to the ventilator, where the conversion devices covert nitrogen dioxide into nitric oxide, and a patient interface operably coupled to the conversion devices, where the patient interface delivers nitric oxide to the patient.

7 Claims, 5 Drawing Sheets

SYSTEMS FOR GENERATING NITRIC OXIDE

CLAIM OF PRIORITY

This application claims the benefit of prior U.S. Provisional Application No. 61/090,616, filed on Aug. 21, 2008, which is incorporated by reference in its entirety.

TECHNICAL FIELD

This description relates to systems for generating nitric oxide.

BACKGROUND

Nitric oxide (NO), also known as nitrosyl radical, is a free radical that is an important signaling molecule. For example, NO causes smooth muscles in blood vessels to relax, thereby resulting in vasodilation and increased blood flow through the blood vessel. These effects are limited to small biological regions since NO is highly reactive with a lifetime of a few seconds and is quickly metabolized in the body.

Typically, NO gas is supplied in a bottled gaseous form diluted in nitrogen gas ($N_2$). Great care has to be taken to prevent the presence of even trace amounts of oxygen ($O_2$) in the tank of NO gas because NO, in the presence of $O_2$, is oxidized into nitrogen dioxide ($NO_2$). Unlike NO, the part per million levels of $NO_2$ gas is highly toxic if inhaled and can form nitric and nitrous acid in the lungs.

SUMMARY

Briefly, and in general terms, various systems generating nitric oxide are disclosed herein. According to one embodiment, the system includes a first gas source providing nitrogen dioxide mixed in air or oxygen, and a second gas source supplying compressed air and/or compressed oxygen. The system also includes a ventilator coupled to the first and second gas sources, wherein the ventilator is resistant to nitrogen dioxide. The ventilator regulates gas flow and allows for the adjustment of nitrogen dioxide concentration in the gas flow. The system further includes one or more conversion devices operably coupled to the ventilator where the conversion devices convert nitrogen dioxide into nitric oxide. A patient interface delivers nitric oxide to the patient and is operably coupled to the conversion devices.

In another embodiment, the system includes a humidifier that is placed prior to the first conversion device. In yet another embodiment, the humidifier is integral with the conversion device. Optionally, the system includes an active humidifier that is placed prior to a second conversion cartridge which is adjacent to the patient interface.

The system allows oxygen and nitric oxide levels to be varied independently. The system also includes safeguards in the event of system failure. In one embodiment, the main conversion cartridge in the system is designed to have sufficient capacity to convert the entire contents of more than one bottle of nitrogen dioxide in the event of system failure. In another embodiment, a second conversion cartridge is also included as a redundant safety measure where the second conversion cartridge is able to convert the entire contents of a bottle of nitrogen dioxide into nitric oxide.

Other features will become apparent from the following detailed description, taken in conjunction with the accompanying drawings, which illustrate by way of example, the features of the various embodiments.

DETAILED DESCRIPTION

Various systems and devices for generating nitric oxide (NO) are disclosed herein. Generally, NO is inhaled or otherwise delivered to a patient's lungs. Since NO is inhaled, much higher local doses can be achieved without concomitant vasodilation of the other blood vessels in the body. Accordingly, NO gas having a concentration of approximately 2 to approximately 1000 ppm (e.g., greater than 2, 20, 40, 80, 100, 150, 200, 250, 300, 350, 400, 450, 500, 550, 600, 650, 700, 750, 800, 850, 900, 950, 1000, 1200, 1400, 1600, 1800 and 2000 ppm) may be delivered to a patient. Accordingly, high doses of NO may be used to prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma, status asthmaticus, or hypoxia. NO can also be used to treat chronic pulmonary hypertension, bronchopulmonary dysplasia, chronic pulmonary thromboembolism, idiopathic pulmonary hypertension, primary pulmonary hypertension, or chronic hypoxia.

Currently, approved devices and methods for delivering inhaled NO gas require complex and heavy equipment, and they are limited in their output to 80 ppm of NO because of the presence of the toxic compound, nitrogen dioxide ($NO_2$). NO gas is stored in heavy gas bottles with nitrogen and no traces of oxygen. NO gas is mixed with air or oxygen with specialized injectors and complex ventilators, and the mixing process is monitored with equipment having sensitive microprocessors and electronics. All this equipment is required in order to ensure that NO is not oxidized into $NO_2$ during the mixing process since $NO_2$ is highly toxic. However, this equipment is not conducive to use in routine hospital and non-medical facility settings since the size, cost, complexity, and safety issues restrict the operation of this equipment to highly-trained professionals who are specially trained in its use.

Figure 1:
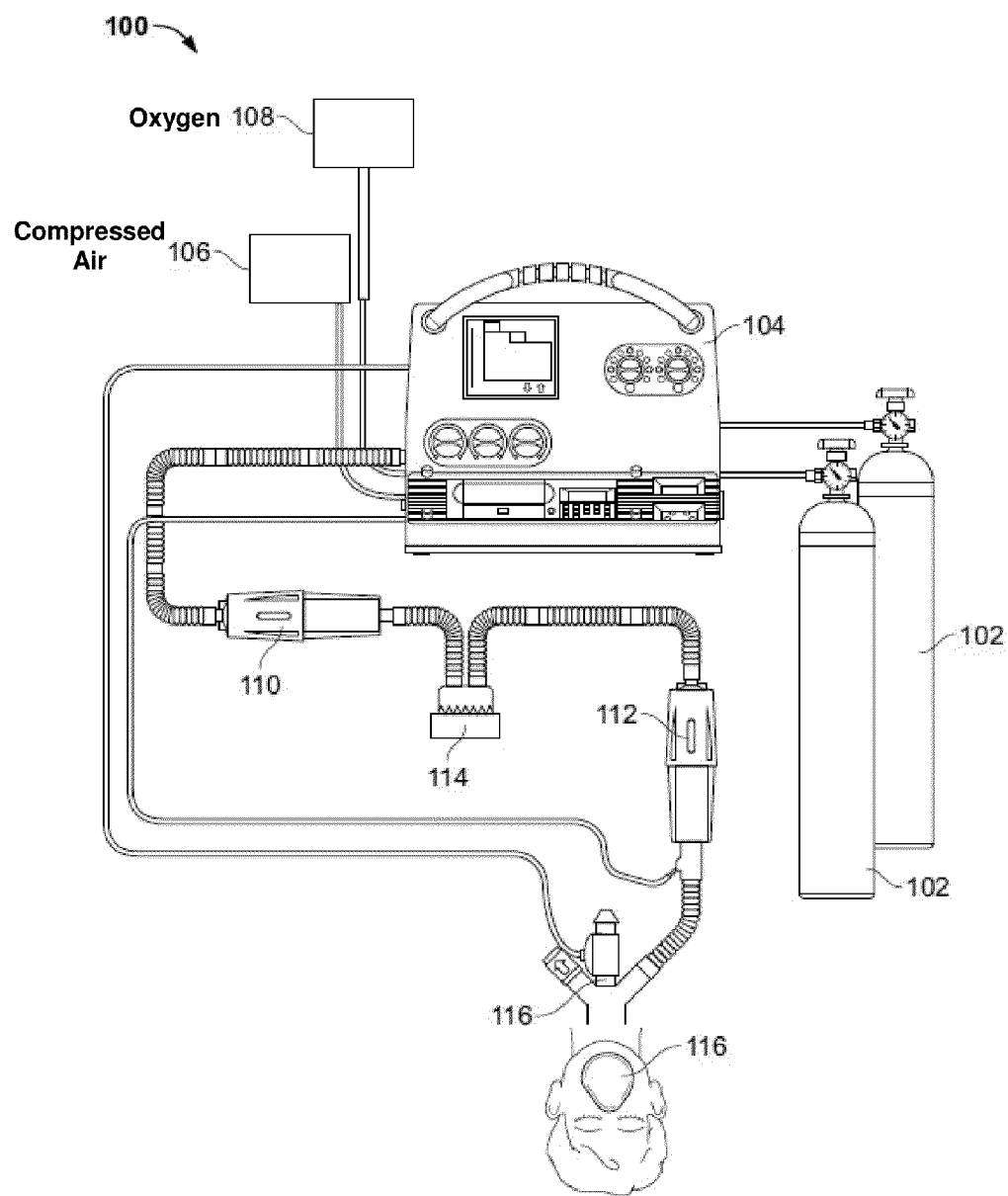
FIG. 1 is a schematic view of one embodiment of a nitric oxide (NO) generating system.
Figure 2:
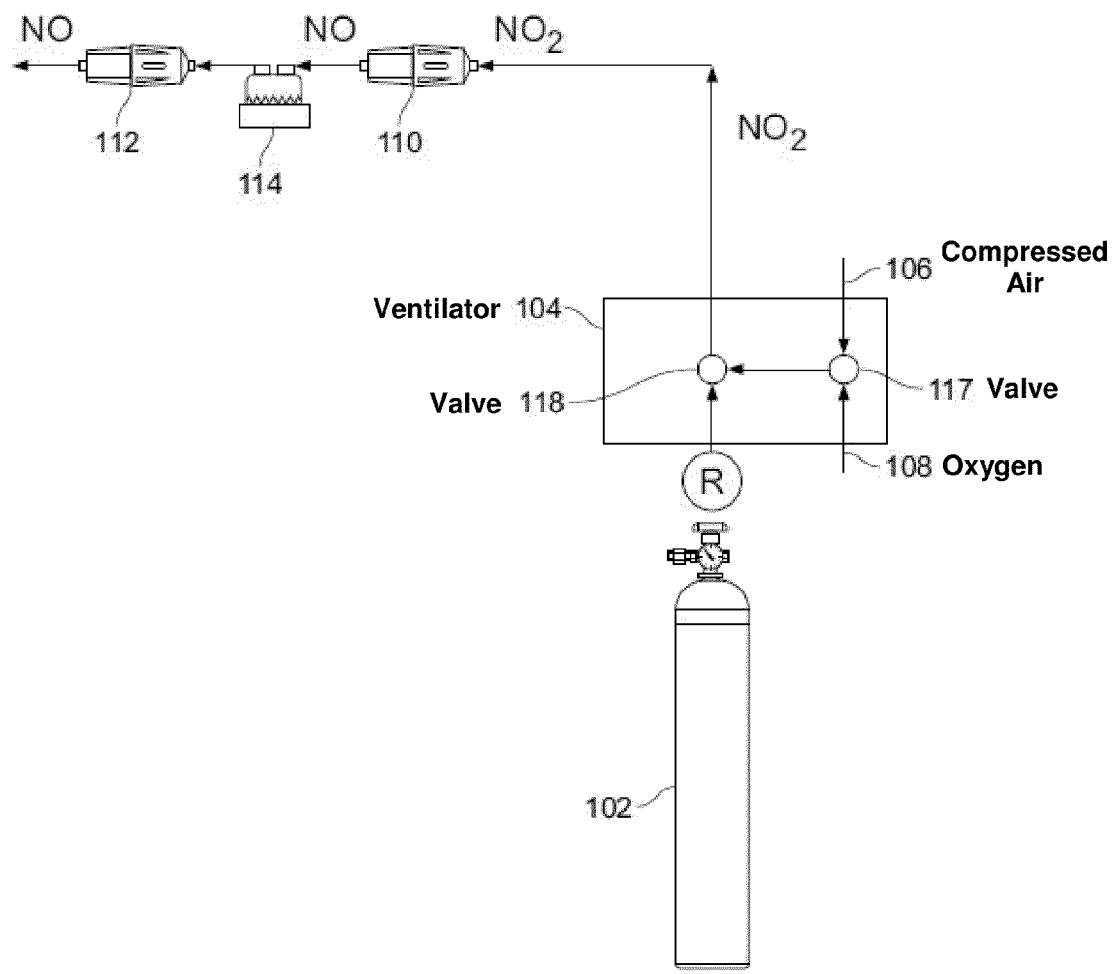
FIG. 2 is a block diagram of one embodiment of a NO generating system.

FIGS. 1-2 illustrate one embodiment of a system 100 that generates NO from $NO_2$. The system 100 may be used in a medical setting such as, but not limited to, an operating theatre or an intensive care unit. The system 100 includes a gas source 102 containing $NO_2$ premixed in air 106 or oxygen 108. As shown in FIG. 1, the system 100 includes two gas sources 102 where one bottle is a standby in the event the first bottle becomes depleted. Alternatively, the system 100 may include a single gas source capable of producing NO. In another embodiment, the system 100 may include a plurality of gas sources capable of producing NO. Optionally, if more than one gas source is provided with the system 100, a valve (not shown) is coupled to the gas sources and allows for switching between the gas sources.

The system 100 includes a ventilator 104 connected to the gas sources 102 capable of producing NO in addition to a gas source of compressed air 106 and oxygen 108, as shown in FIG. 1. The ventilator 104 also includes components such as mixing valves 117, 118 that are resistant to $NO_2$ gas. In one embodiment, the mixing valves 117, 118 used in the ventilator 102 are manufactured by Bio-Med Devices of Guilford, Conn. The ventilator 104 is also provided with controls to independently vary the concentration of $NO_2$ and oxygen 108. Accordingly, the mixing valves 117, 118 and the ventilator 104 regulate and adjust the concentration of the gas so that it is at a proper concentration to be converted into a therapeutic dose of NO at the main conversion cartridge 110. Additionally, the ventilator 104 can be adjusted to provide the proper gas flow pattern.

As shown in FIGS. 1-2, the gas passes through the main conversion cartridge 110 where $NO_2$ in the gas flow is converted to NO. In one embodiment, a passive humidifier (not shown) is positioned to the main cartridge 110. The passive humidifier operates at a dew point of approximately less than 18° C. (not shown) that may be separate or integral with the main cartridge 110. The NO gas generated by the main conversion cartridge 110 then flows through an active humidifier 114, which provides moisture to the patient and also extends the lifespan of the conversion cartridge 112. The humidified NO gas then filters through a secondary cartridge 112 (also referred to as a recuperator) to convert any $NO_2$ in the gas lines into NO. The NO gas (in air or oxygen) is then delivered to a patient via a patient interface 116. The patient interface 116 may be a mouth piece, nasal cannula, face mask, or fully-sealed face mask. The active humidifier brings the moisture content of the NO gas (and air/oxygen) up to a dew point of approximately 32 to 37° C., thereby preventing moisture loss from the lungs.

As shown in FIGS. 1-2, a single humidifier 114 is positioned between the conversion cartridges 110, 112. In another embodiment, the system 100 may include humidifiers 114 placed prior to each conversion cartridge 110, 112. As shown in FIGS. 1-2, the humidifier 114 is a separate device, but it is contemplated that the humidifier may be an integral component of each conversion cartridge (not shown). According to one embodiment, the humidifier 114 used in the system 100 is manufactured by Fisher and Pykell.

Additionally, the system 100 may include one or more safety features. In one embodiment, the main conversion cartridge 110 is sized so that it has excess capacity to convert $NO_2$ into NO. For example, the main conversion cartridge 110 is sized to convert the entire contents of more than one gas source 102 of $NO_2$ gas. If the main conversion cartridge 110 were to fail, the recuperator cartridge 112 has sufficient capacity to convert the entire contents of a gas bottle 102. In yet another embodiment, $NO_2$ and the NO gas concentrations may be monitored after the main conversion cartridge 110. In one embodiment, the gas concentrations of NO and $NO_2$ may be monitored by one or more NO and $NO_2$ detectors manufactured by Cardinal Healthcare, Viasys Division. If any $NO_2$ is detected, visual and/or auditory alarms would be presented to the operator. The alarms will allow the operator to correct the problem, but the recuperator cartridge 112 would convert any $NO_2$ that was present in the gas lines back into NO. This function is important at very high NO levels (>40 ppm) as well as during start up of the system 100. Additionally, the recuperator cartridge 112 makes it unnecessary to flush the lines to remove $NO_2$, since the $NO_2$ in the lines would be converted to NO by the recuperator prior to delivery to a patient.

Figure 3:
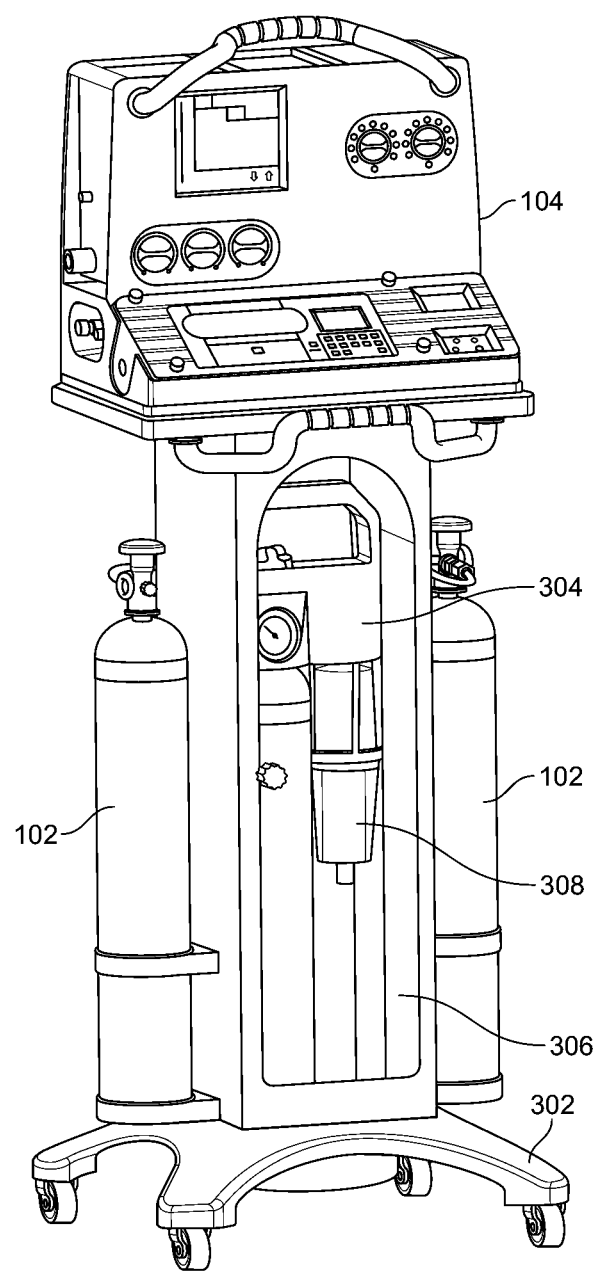
FIG. 3 is a perspective view of one embodiment of a system for delivering NO to a patient.

FIG. 3 illustrates another embodiment of a system 300 for delivering NO to a patient. The system 300 is provided on a wheeled stand 302. The system 300 includes a ventilator 104 that is resistant to $NO_2$ gas. The system 300 also includes two gas sources 102 for providing $NO_2$ gas. Additionally, a third gas source 306 is also mounted in the center of the stand 302. The third gas source 306 contains $NO_2$ in air or oxygen at an appropriate concentration. The third gas source 306 is also connected to the ventilator 104 by gas plumbing 304 and is in a standby mode. In the event of a disruption of the $NO_2$ gas, compressed air, or compressed oxygen, an automatic series of valves would shut down the feed of gas to the ventilator 104 and replace it with gas from the back up gas source 306. This safety feature is on standby mode and may be implemented within the time frame of a single breath. If the ventilator 104 malfunctions, the third gas source 306 is available as substitute for the system 300. The third gas source 306 includes a NO conversion cartridge 308 and may be used to deliver NO to the patient by means of a handheld ventilator (not shown).

Conversion Cartridges

Figure 4:
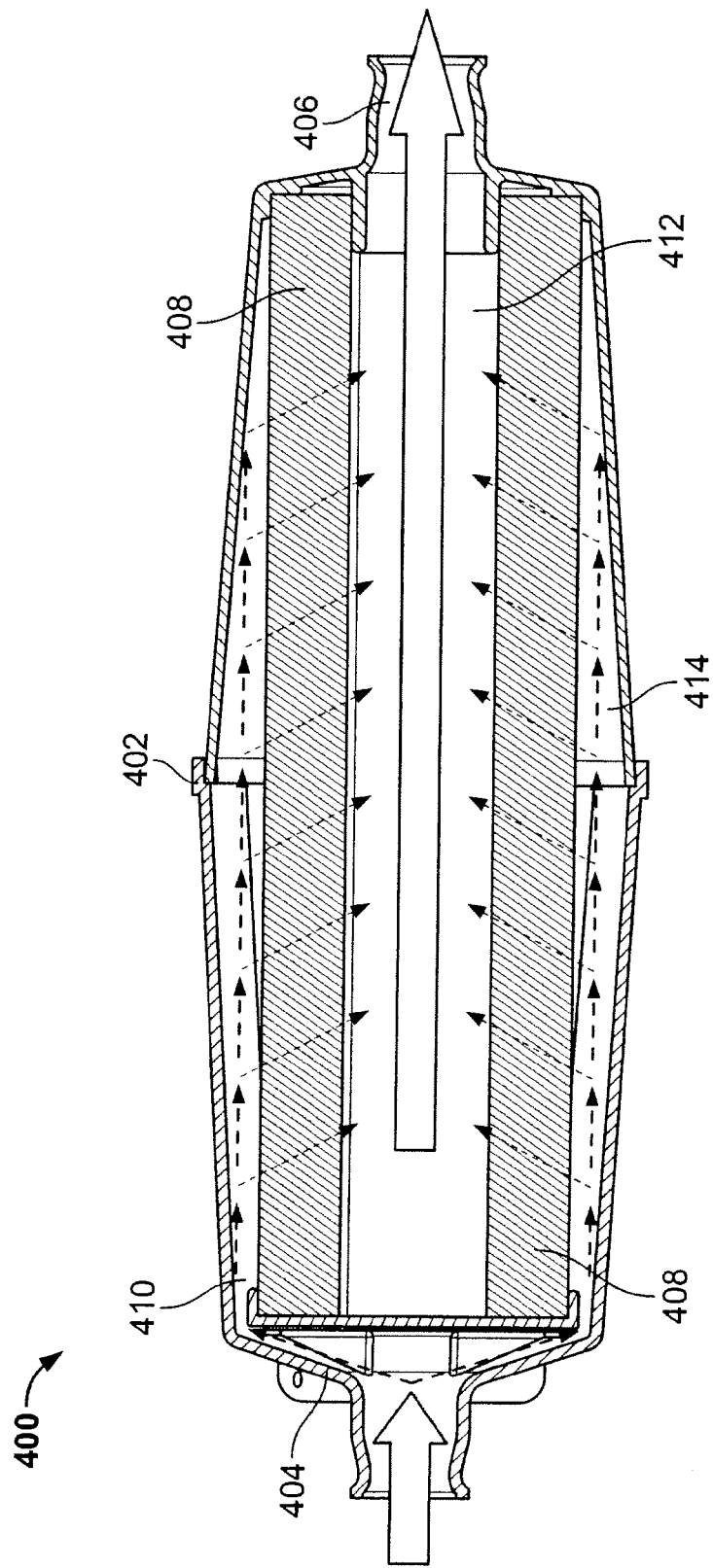
FIG. 4 is a cross-sectional view of one embodiment of a NO generating device.

FIG. 4 illustrates one embodiment of a device 400 that generates NO from $NO_2$. The device 100, which may be referred to as a NO generation cartridge, a GENO cartridge, a GENO cylinder, or a recuperator, includes a body 402 having an inlet 404 and an outlet 406. The inlet 404 and outlet 406 are sized to engage gas plumbing lines or directly couple to other components such as, but not limited to, gas tanks, regulators, valves, humidifiers, patient interfaces, or recuperators. Additionally, the inlet 404 and outlet 406 may include threads or specially designed fittings to engage these components.

As shown in FIG. 4, the body 402 is generally cylindrical in shape and defines a cavity that holds a porous solid matrix 408. According to one embodiment, the porous solid matrix 408 is a mixture of a surface-activated material such as, but not limited to, silica gel and one or more suitable thermoplastic resins. The thermoplastic resin, when cured, provides a rigid structure to support the surface-activated material. Additionally, the porous thermoplastic resin may be shaped or molded into any form.

According to one embodiment, the porous solid matrix 408 is composed of at least 20% silica gel. In another embodiment, the porous solid matrix 408 includes approximately 20% to approximately 60% silica gel. In yet another embodiment, the porous solid matrix 408 is composed of 50% silica gel. As those skilled in the art will appreciate, any ratio of silica gel to thermoplastic resin is contemplated so long as the mechanical and structural strength of the porous solid matrix 408 is maintained. In one embodiment, the densities of the silica gel and the thermoplastic resin are generally similar in order to achieve a uniform mixture and, ultimately, a uniform porous solid matrix 408.

As shown in FIG. 4, the porous solid matrix 408 also has a cylindrical shape having an inner bore 412. In other embodiments, the porous solid matrix may have any shape known or developed in the art. The porous solid matrix 408 is positioned within the body 402 such that a space 414 is formed between the body and the porous solid matrix 408. At the inlet end 404 of the body 402, a diverter 410 is positioned between the inlet and the porous solid matrix 408. The diverter 410 directs the gas flow to the outer diameter of the porous solid matrix 408 (as shown by the white arrows). Gas flow is forced through the porous solid matrix 408 whereby any $NO_2$ is converted into NO (as shown by the darkened arrows). NO gas then exits the outlet 406 of the device 400. The porous solid matrix 408 allows the device 400 to be used in any orientation (e.g., horizontally, vertically, or at any angle). Additionally, the porous solid matrix 408 provides a rigid structure suitable to withstand vibrations and abuse associated with shipping and handling.

Figure 5:
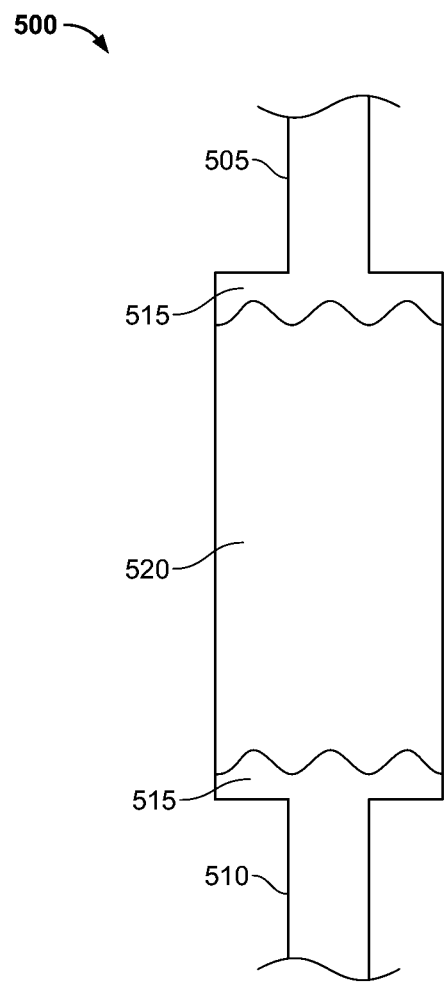
FIG. 5 is a block diagram of another embodiment of a NO generating device.

FIG. 5 illustrates another embodiment of a conversion cartridge 500 that generates NO from $NO_2$. The conversion cartridge 500 includes an inlet 505 and an outlet 510. Porous filters or a screen and glass wool 515 are located at both the inlet 505 and the outlet 510, and the remainder of the cartridge 500 is filled with a surface-active material 520 that is soaked with a saturated solution of antioxidant in water to coat the surface-active material. In the example of FIG. 5, the antioxidant is ascorbic acid.

In a general process for converting $NO_2$ to NO, an air flow having $NO_2$ is received through the inlet 505 and the air flow is fluidly communicated to the outlet 110 through the surface-active material 520 coated with the aqueous antioxidant. As long as the surface-active material remains moist and the antioxidant has not been used up in the conversion, the general process is effective at converting $NO_2$ to NO at ambient temperatures.

The inlet 505 may receive the air flow having $NO_2$, for example, from a pressurized bottle of $NO_2$, which also may be referred to as a tank of $NO_2$. The inlet 505 also may receive an air flow with $NO_2$ in nitrogen ($N_2$), air, or oxygen ($O_2$). The inlet 505 may also receive the air flow having $NO_2$ from an air pump that fluidly communicates an air flow over a permeation or a diffusion tube (not shown). The conversion occurs over a wide concentration range. Experiments have been carried out at concentrations in air of from about 0.2 ppm $NO_2$ to about 100 ppm $NO_2$, and even to over 1000 ppm $NO_2$. In one example, a cartridge that was approximately 5 inches long and had a diameter of 0.8-inches was packed with silica gel that had first been soaked in a saturated aqueous solution of ascorbic acid. Other sizes of the cartridge are also possible. The moist silica gel was prepared using ascorbic acid (i.e., vitamin C) designated as A.C.S. reagent grade 99.1% pure from Aldrich Chemical Company and silica gel from Fischer Scientific International, Inc., designated as S8 32-1, 40 of Grade of 35 to 70 sized mesh. Other sizes of silica gel also are effective as long as the particles are small enough and the pore size is such as to provide sufficient surface area.

The silica gel was moistened with a saturated solution of ascorbic acid that had been prepared by mixing 35% by weight ascorbic acid in water, stirring, and straining the water/ascorbic acid mixture through the silica gel, followed by draining. In one embodiment, the silica gel is dried to about 30% moisture by weight. It has been found that the conversion of $NO_2$ to NO proceeds well when the silica gel coated with ascorbic acid is moist. The conversion of $NO_2$ to NO does not proceed well in an aqueous solution of ascorbic acid alone.

The cartridge filled with the moist silica gel/ascorbic acid was able to convert 1000 ppm of $NO_2$ in air to NO at a flow rate of 150 ml per minute, quantitatively, non-stop for over 12 days. A wide variety of flow rates and $NO_2$ concentrations have been successfully tested, ranging from only a few ml per minute to flow rates of up to approximately 5,000 ml per minute, up to flow rates of approximately 80,000 ml per minute. The reaction also proceeds using other common antioxidants, such as variants of vitamin E (e.g., alpha tocopherol and gamma tocopherol).

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. A system for delivering nitric oxide to a patient, comprising:
   a first gas source including nitrogen dioxide premixed in air or oxygen;
   a second gas source supplying compressed air;
   a ventilator coupled to the first and second gas sources;
   a mixing valve which is connected to both the first gas source and the second gas source downstream of both the first gas source and the second gas source, wherein the mixing valve is resistant to $NO_2$ gases;
   one or more conversion devices operably coupled to the ventilator, wherein the one or more conversion devices include
   an inlet,
   a chamber containing a matrix, wherein the matrix is positioned within the chamber and a space between the chamber and the matrix, and
   a diverter positioned between the inlet and the chamber, wherein the diverter is configured to direct a gas flow to the space between the chamber and the matrix, and wherein the one or more conversion devices convert nitrogen dioxide into nitric oxide; and
   a patient interface operably coupled to the one or more conversion devices, wherein the patient interface delivers nitric oxide to the patient.

2. The system of claim 1, further comprising a third gas source supplying compressed oxygen, wherein the third gas source is in communication with the ventilator.

3. The system of claim 1, further comprising a humidifier positioned between the ventilator and the one or more conversion devices.

4. The system of claim 1, comprising a first conversion device of the one or more conversion devices, wherein a humidifier is integral with the first conversion device.

5. The system of claim 1, comprising a first conversion device of the one or more conversion devices and a second conversion device of the one or more conversion devices, wherein a humidifier is integral with the second conversion device.

6. The system of claim 1, comprising a first conversion device of the one or more conversion devices, a second conversion device of the one or more conversion devices and a humidifier, wherein the humidifier is positioned between the first conversion device and the patient interface and before the second conversion device.

7. The system of claim 1, wherein the mixing valve is within the ventilator.

* * * * *